(12) United States Patent
Ferrara et al.

(10) Patent No.: US 9,765,326 B2
(45) Date of Patent: Sep. 19, 2017

(54) APPARATUS AND METHOD FOR NUCLEIC ACID SEQUENCING BASED ON NANOCHANNELS

(71) Applicant: STMICROELECTRONICS S.R.L., Agrate Brianza (IT)

(72) Inventors: Francesco Ferrara, Monteroni di Lecce (IT); Marco Angelo Bianchessi, Melzo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 120 days.

(21) Appl. No.: 14/676,626

(22) Filed: Apr. 1, 2015

(65) Prior Publication Data

US 2015/0284707 A1 Oct. 8, 2015

(30) Foreign Application Priority Data

Apr. 3, 2014 (IT) .............................. TO2014A0279

(51) Int. Cl.
*G01N 27/447* (2006.01)
*C12N 15/10* (2006.01)
(Continued)

(52) U.S. Cl.
CPC ...... *C12N 15/101* (2013.01); *B01L 3/502761* (2013.01); *C12Q 1/6869* (2013.01);
(Continued)

(58) Field of Classification Search
CPC ................ C12N 15/101; C12Q 1/6869; C12Q 2523/307; C12Q 2563/157;
(Continued)

(56) References Cited

U.S. PATENT DOCUMENTS 8,607,632 B2 12/2013 Meisel et al.
8,673,627 B2 3/2014 Nobile et al.
(Continued)

FOREIGN PATENT DOCUMENTS

CN 103275867 A 9/2013
EP 1 441 213 A1 7/2004
(Continued)

OTHER PUBLICATIONS

"DNA: An introduction to nanopore sequencing," Nanopore™ Techologies, retrieved from https://nanoporetech.com/technology/analytes-and-applications-dna-rna-proteins/dna-an-introduction-to-nanopore-sequencing, on Sep. 4, 2014, 2 pages.
(Continued)

*Primary Examiner* — J. Christopher Ball
(74) *Attorney, Agent, or Firm* — Seed IP Law Group LLP

(57) ABSTRACT

An apparatus for nucleic acid sequencing includes a nanochannel and a conveying device, configured to move a nucleic acid strand through the nanochannel. The conveying device includes: a first electrode, a second electrode, and a third electrode, which are arranged along the nanochannel so as to be in contact with a fluid occupying the nanochannel, the second electrode being arranged between the first electrode and the third electrode; and a control unit configured to apply a first voltage, a second voltage, and a third voltage, respectively, to the first electrode, the second electrode and the third electrode, for controlling movement of the nucleic acid strand through the nanochannel.

25 Claims, 5 Drawing Sheets

(51) Int. Cl.
*B01L 3/00* (2006.01)
*G01N 33/487* (2006.01)
*C12Q 1/68* (2006.01)

(52) U.S. Cl.
CPC . *G01N 27/44791* (2013.01); *G01N 33/48721* (2013.01); *B01L 2200/0652* (2013.01); *B01L 2300/0627* (2013.01); *C12Q 2523/307* (2013.01); *C12Q 2563/157* (2013.01); *C12Q 2565/607* (2013.01)

(58) Field of Classification Search
CPC ........ C12Q 2563/607; G01N 33/48721; B01L 3/502761; B01L 2200/0652; B01L 2300/0627
See application file for complete search history.

(56) References Cited

U.S. PATENT DOCUMENTS

| | | | |
|---|---|---|---|
| 8,882,980 | B2 | 11/2014 | Ling et al. |
| 2003/0215816 | A1 | 11/2003 | Sundararajan et al. |
| 2006/0246497 | A1 | 11/2006 | Huang et al. |
| 2006/0275911 | A1 | 12/2006 | Wang et al. |
| 2008/0187915 | A1 | 8/2008 | Polonsky et al. |
| 2010/0078325 | A1* | 4/2010 | Oliver .............. G01N 33/48721 204/452 |
| 2011/0236984 | A1 | 9/2011 | Sun et al. |
| 2012/0264617 | A1 | 10/2012 | Pettit |
| 2013/0213815 | A1 | 8/2013 | Tung et al. |
| 2014/0193820 | A1 | 7/2014 | Sun et al. |
| 2015/0218630 | A1 | 8/2015 | Sun et al. |
| 2016/0274056 | A1 | 9/2016 | Rothberg et al. |

FOREIGN PATENT DOCUMENTS

| | | |
|---|---|---|
| EP | 1 645 628 A1 | 4/2006 |
| EP | 2 311 975 A1 | 4/2011 |
| WO | 02/31183 A1 | 4/2002 |
| WO | 2010/026488 A2 | 3/2010 |
| WO | 2013/012881 A2 | 1/2013 |
| WO | 2013/088098 A2 | 6/2013 |
| WO | 2014/059046 A1 | 4/2014 |

OTHER PUBLICATIONS

"Nanopore Group—About: Home," UC Santa Cruz, retrieved from http://nanopore.bme.ucsc.edu/about, on Sep. 4, 2014, 2 pages.

Branton et al., "The potential and challenges of nanopore sequencing," *Nature Biotechnology* 26(10):1146-1153, Oct. 2008.

Davies, "Oxford Strikes First in DNA Sequencing Nanopore Wars," Feb. 17, 2012, retrieved from http://www.bio-itworld.com/news/02/17/12/Oxford-strikes-first-in-DNA-sequencing-nanopore-wars.html, on Sep. 4, 2014, 3 pages.

Gao et al., "Silicon Nanowire Arrays for Label-Free Detection of DNA," *Anal. Chem.* 79(9):3291-3297, May 2007.

Gen, "Roche and IBM Set Sights on $100-1,000 Genome Nanopore Sequencing Platform," Jul. 1, 2010, retrieved from http://www.genengnews.com/gen-news-highlights/roche-and-ibm-set-sights-on-100-1-000-genome-nanopore-sequencing-platform/81243603/, on Sep. 4, 2014, 2 pages.

Iganacio-de Leon et al., "Size-selective molecular transport through silica colloidal nanopores," *Chem. Commun.* 47:553-555, 2011.

Karger et al., "Multiwavelength fluorescence detection for DNA sequencing using capillary electrophoresis," *Nucleic Acids Research* 19(18):4955-4962, 1991.

Kim et al., "An FET-type charge sensor for highly sensitive detection of DNA sequence," *Biosensors and Bioelectronics* 20:69-74, 2004.

Kumemura et al., "Single DNA Molecule Isolation and Trapping in a Microfluidic Device," *ChemPhysChem* 8:1875-1880, 2007.

LabGrab, "New DNA Sequencing Method Increases Speed While Decreasing Costs," Dec. 22, 2009, retrieved from http://www.labgrab.com/users/labgrab/blog/new-dna-sequencing-method-increases-speed-while-decreasing-costs, on Mar. 23, 2015, 2 pages.

Li et al., "Electrically moving single-stranded DNA into and out of double-walled carbon nanotubes," *Chem. Commun.* 47:2309-2311, 2011.

Liu et al., "Voltage-Driven Translocation of DNA through a High Throughput Conical Solid-State Nanopore," *PLOS ONE* 7(9) e46014:1-9, Sep. 2012.

Paulasova, P. et al., "The peptide nucleic acids (PNAs): a new generation of probes for genetic and cytogenetic analyses," Annales de Genetique, vol. 47, pp. 349-358, 2004.

Pollack, "Company Unveils DNA sequencing Device Meant to Be Portable, Disposable and Cheap," Feb. 17, 2012, The New York Times, retrieved from http://www.nytimes.com/2012/02/18/health/oxford-nanopore-unveils-tiny-dna-sequencing-device.html, on Sep. 4, 2014, 2 pages.

Pooga, M. et al., "PNA oligomers as tools for specific modulation of gene expression," Biomolecular Engineering, vol. 17, pp. 183-193, 2001.

Schaffer, "Nanopore Sequencing: Simple and direct analysis of DNA will make genetic testing routine in more situations.," May/Jun. 2012, MIT Technology Review, retrieved from http://www2.technologyreview.com/article/427677/nanopore-sequencing/, on Sep. 4, 2014, 2 pages.

Seong et al., "Single-Molecular AFM Probing of Specific DNA Sequencing Using RecA-Promoted Homologous Pairing and Strand Exchange," *Anal. Chem.* 72(6):1288-1293, Mar. 2000.

Tsutsui et al., "Transverse electric field dragging of DNA in a nanochannel," *Scientific Reports* 2(394):1-7, May 2012.

Wanunu, "Nanopores: A journey towards DNA sequencing," *Physics of Life Reviews* 2(9):125-158, May 2012.

Zhang et al., "Highly sensitive measurements of PNA-DNA hybridization using oxide-etched silicon nanowire biosensors," *Biosensors and Bioelectronics* 23:1701-1707, 2008.

* cited by examiner

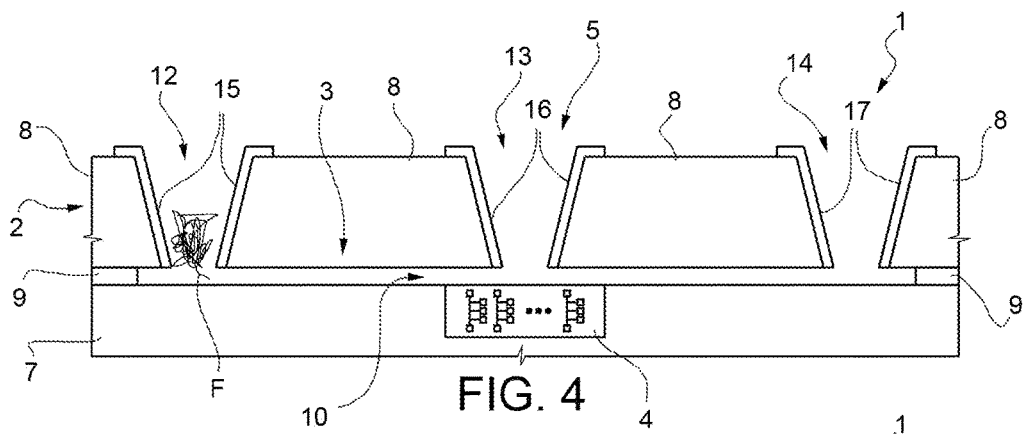
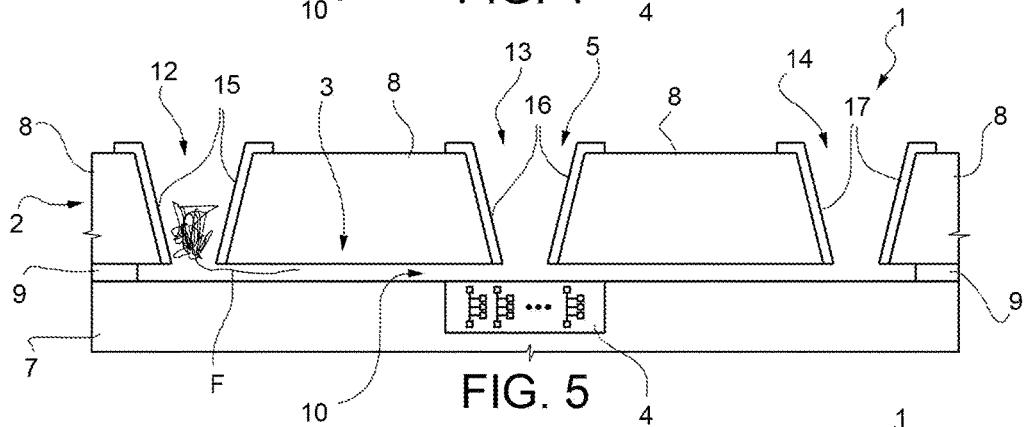
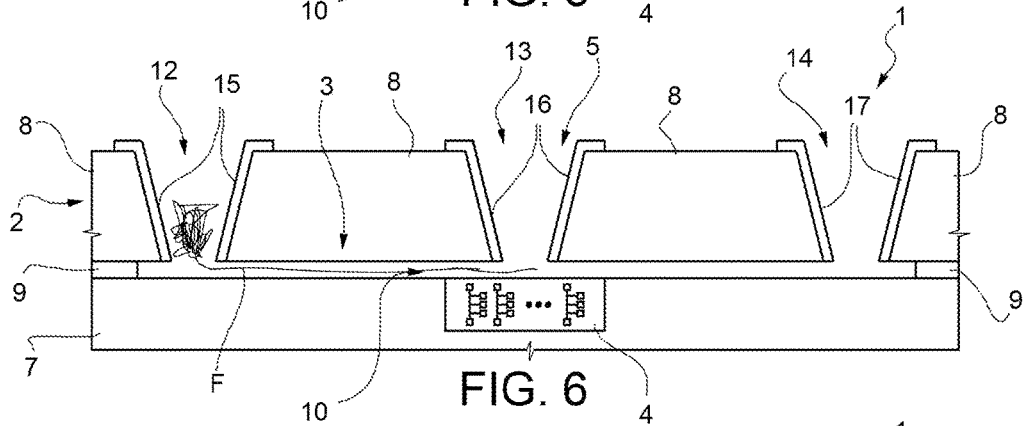
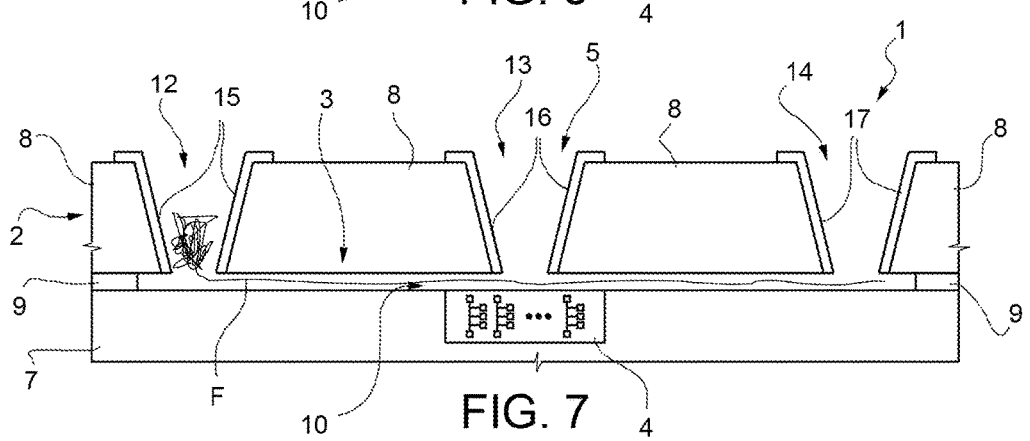

APPARATUS AND METHOD FOR NUCLEIC ACID SEQUENCING BASED ON NANOCHANNELS

BACKGROUND

Technical Field

The present disclosure relates to an apparatus and to a method for nucleic acid sequencing based on nanochannels.

Description of the Related Art

Given the ever-increasing importance that nucleic acid sequencing is assuming, various techniques have been developed for determining the nucleotide sequence.

Some of the known techniques are based upon the division of a nucleic acid molecule into short fragments, in general of some hundreds of bases, which are sequenced individually. The information collected on the individual portions is subsequently processed and aggregated for reconstructing the entire sequence of the bases that form the nucleic acid molecule. Reconstruction of the sequence is, however, an operation that is extremely complex and consuming in terms of resources, in particular, processing capacity, and time. Furthermore, it may happen that some fragments are not read and reconstructed correctly, and thus sequencing may be incomplete.

The developments in the nanotechnology sector have enabled development of new devices and techniques that enable handling of individual molecules, by exploiting, in particular, the electrical charge with which the nucleic acids are provided. For instance, in some devices appropriate electrical fields are used to cause passage of a single nucleic acid molecule through a nanopore in a membrane. In practice, the device has two chambers separated by a membrane, which has a nanopore and is provided with electrodes that enable creation of an electrical field. A solution containing molecules of a nucleic acid is loaded into one of the two chambers. Then, one end of a nucleic acid molecule, which normally presents as an entangled strand, may be introduced into the nanopore thanks to the electrical field. The dimensions of the nanopore are such that the presence of a portion of one molecule inhibits entry of ends of further molecules (the diameter of the nanopore may, for example, be between 5 nm and 10 nm). In this way, it is possible to isolate and handle a single sequence. The force exerted by the electrical field causes the strand forming the molecule to extend as it passes through the nanopore following after the end. The strand thus extended may be analyzed for sequencing.

Examples of devices of this type are described in Liu Q., Wu H., Wu L., Xie X., Kong J., et al. (2012), "Voltage-Driven Translocation of DNA through a High Throughput Conical Solid-State Nanopore", PLoS ONE 7(9): e46014; DOI:10.1371/journal.pone.0046014; and in Tsutsui, M. et al., "Transverse Electric Field Dragging of DNA in a Nanochannel" Sci. Rep. 2, 394; DOI:10.1038/srep00394 (2012).

A limitation linked to the known devices lies in the low flexibility in controlling sliding of the strand through the nanopore and the forces exerted thereon. Since the accuracy in identifying the correct sequence of the bases depends markedly also upon these parameters, it is evident that fine control is decisive to obtain reliable results and efficient procedures of analysis.

BRIEF SUMMARY

Some embodiments of the present disclosure provide an apparatus and a method for nucleic acid sequencing that will enable the limitations described to be overcome.

One embodiment of the present disclosure is an apparatus for nucleic acid sequencing. The apparatus includes a nanochannel and a conveying device configured to move a nucleic acid strand through the nanochannel. The conveying device comprises first, second, and third electrodes arranged along the nanochannel so as to be in contact with a fluid occupying the nanochannel, the second electrode being arranged between the first and third electrodes. The conveying device also includes a control unit configured to apply a first, second, and third voltages to the first, second, and third electrodes, respectively, and thereby control movement of the nucleic acid strand through the nanochannel.

BRIEF DESCRIPTION OF THE SEVERAL VIEWS OF THE DRAWINGS

For a better understanding of the disclosure, some embodiments thereof will now be described, purely by way of non-limiting example and with reference to the attached drawings, wherein:

FIGS. 4-7 show the cross-section of FIG. 1 in respective operating configurations;

DETAILED DESCRIPTION

Figure 1:
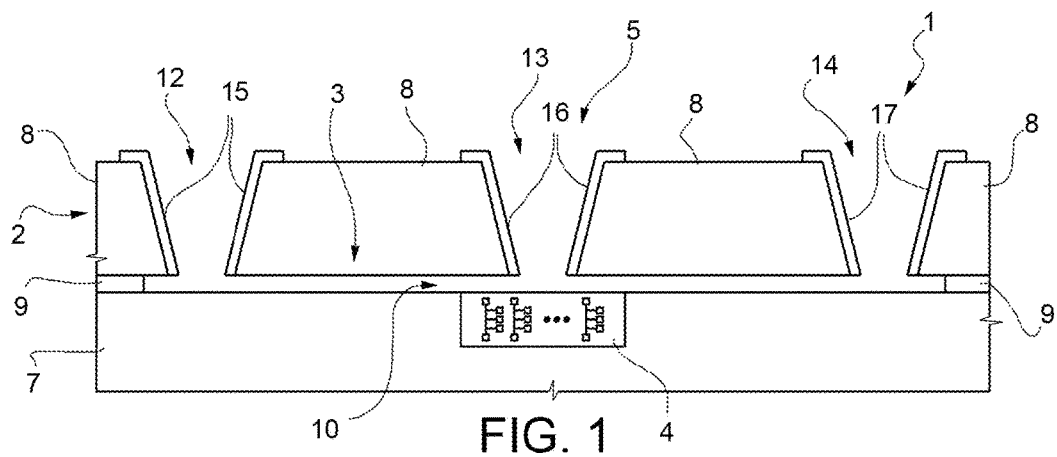
FIG. 1 is a cross-section through a body integrating a portion of an apparatus for nucleic acid sequencing according to an embodiment of the present disclosure.
Figure 2:
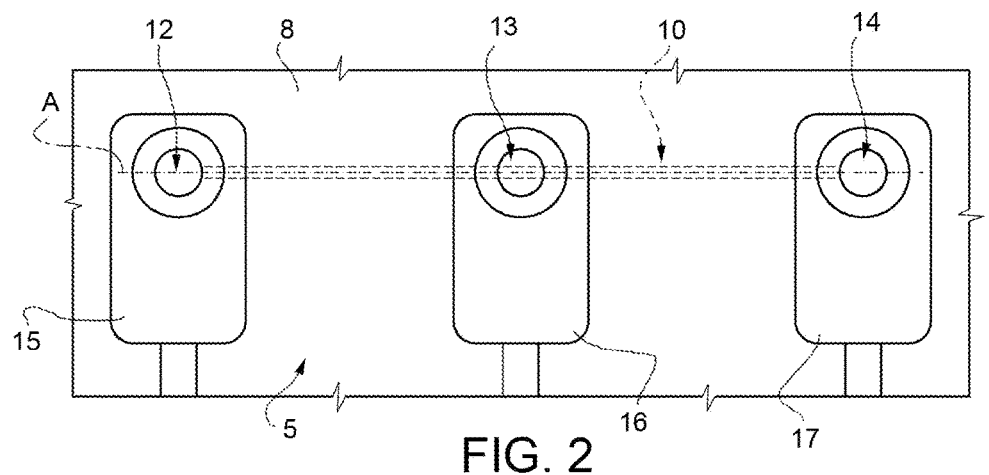
FIG. 2 is a top plan view of the body of FIG. 1.

With reference to FIGS. 1 and 2, an apparatus for nucleic acid sequencing is designated as a whole by the number 1 and comprises a body 2 housing a fluidic circuit 3, a base-detection device 4, and a conveying device 5, configured to control movement of nucleic acid strands in the fluidic circuit 3.

In one embodiment, the body 2 comprises a first, supporting, structural layer 7 and a second structural layer 8, arranged between which is a spacer layer 9 of nanometric thickness (for example, less than 20 nm). The first structural layer 7 may, for example, be a substrate of intrinsic semiconductor material, or else may be of polymeric material or some other non-conductive material. Alternatively, the first structural layer 7 could also be of a doped semiconductor material and be electrically insulated from the fluidic circuit 3, for example by a dielectric layer delimiting the fluidic circuit 3 itself. The second structural layer 8 and the spacer layer 9 may be, for example, respectively, of aluminum nitride (or else of intrinsic silicon or some other non-conductive or conductive material insulated from the fluidic circuit 3) and of silicon oxide.

In use, the fluidic circuit 3 is filled with a solution containing denatured strands of a nucleic acid and comprises a nanochannel 10, which, in one embodiment, is defined between the first structural layer 7 and the second structural layer 8. Denaturing may be obtained also directly in the fluidic circuit 3, upstream of the inlet of the nanochannel 10. The nanochannel 10 extends longitudinally along an axis A for a length of, for example, between 100 μm and 500 μm and has a cross-section, perpendicular to the axis A, of nanometric dimensions, in particular, less than 100 nm (for example 20×20 nm). Specifically, the transverse dimensions of the nanochannel 10, in a direction perpendicular to its length, are selected for favoring passage of a single extended strand of nucleic acid, as in the case of the nanopores described in the articles cited above. In the example described herein, the nanochannel 10 has a height and a width equal to the thickness of the spacer layer 9. In other embodiments not shown, however, the nanochannel 10 may have a different cross-section, for example rectangular, triangular, or circular.

The fluidic circuit 3 comprises an inlet well 12, a control well 13, and a collection well 14, all defined by respective openings through the second structural layer 8. In particular, the nanochannel 10 is accessible from outside through the inlet well 12 to enable introduction of the solution to be analyzed.

Techniques for providing nanometric fluidic structures, in particular, nanochannels, are known, for example from the published patent application No. US 2013/0213815 A1.

Figure 3:
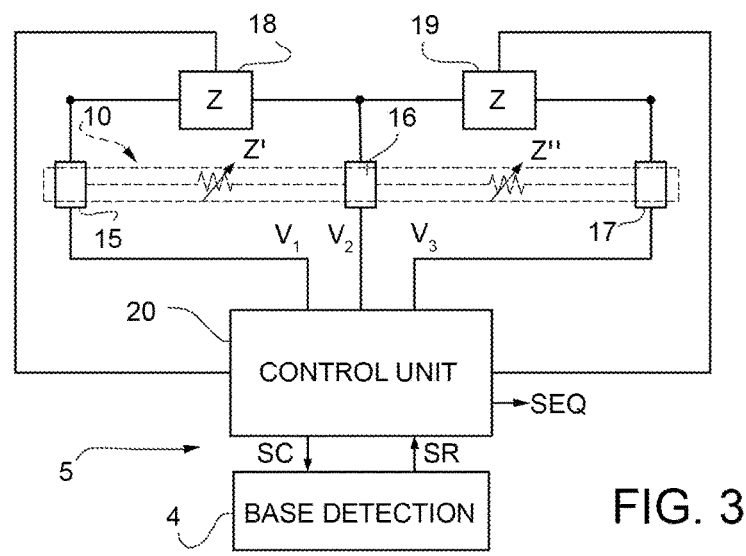
FIG. 3 is a block diagram of the apparatus of FIG. 1.

The conveying device 5 (see also FIG. 3) comprises: a first electrode 15, a second electrode 16, and a third electrode 17, which are arranged along the fluidic circuit 3 and are configured to apply respective voltages to a fluid present in the fluidic circuit 3; a first impedance-meter stage 18 and a second impedance-meter stage 19; and a control unit 20.

In one embodiment, the first electrode 15, the second electrode 16, and the third electrode 17 are arranged on a face of the second structural layer 8 opposite to the first structural layer 7 and coat the side walls, respectively, of the inlet well 12, of the control well 13, and of the collection well 14. In particular, the first electrode 15, the second electrode 16, and the third electrode 17 extend substantially as far as the nanochannel 10 for coming into contact with the solution loaded into the nanochannel 10 itself.

The base-detection device 4 is located in a detection site along the nanochannel 10 in the proximity of the second electrode 16, so as to interact with an extended strand of nucleic acid, advancing in the nanochannel 10 in the detection site. The base-detection device 4 is configured to recognize individual bases or sequences of a programmed number of bases (for example four) in a portion of the strand that is advancing in the detection site. The raw sequence of the bases recognized by the base-detection device 4 is supplied to the control unit 20, which, if necessary, orders the raw sequence into an effective base sequence SEQ (FIG. 3) as explained in detail hereinafter, in order to take into account the detection modality and possible geometrical constraints of the base-detection device 4.

The first impedance-meter stage 18 and the second impedance-meter stage 19 are connected for measuring, respectively, an electrical impedance Z' between the first electrode 15 and the second electrode 16 and an electrical impedance Z" between the second electrode 16 and the third electrode 17. The values of impedance Z', Z" measured are determined by the state of the nanochannel 10 and are supplied to the control unit 20. More precisely, the electrical impedance in a stretch of the nanochannel 10 containing the solution increases when a portion of a nucleic acid strand is present. The first impedance-meter stage 18 and the second impedance-meter stage 19 thus operate as presence sensors that detect the presence of a nucleic acid strand, respectively, in a first portion of the nanochannel 10, between the second electrode 16 and the first electrode 15, and in a second portion of the nanochannel 10, between the third electrode 17 and the second electrode 16. In other embodiments (not illustrated), presence sensors of a different type may be used.

The control unit 20 sets a first voltage $V_1$ on the first electrode 15, a second voltage $V_2$ on the second electrode 16, and a third voltage $V_3$ on the third electrode 17 as a function of the first impedance value Z' and of the second impedance value Z", respectively supplied by the first impedance-meter stage 18 and by the second impedance-meter stage 19.

As described in what follows, the voltages $V_1$, $V_2$, $V_3$ are each time selected on the basis of the impedance values Z', Z" so as to:

favor introduction of one end of a nucleic acid strand F into the nanochannel 10;

counter entry of further strands into the nanochannel 10 when this is already occupied;

control the speed and direction of advance of the strand F present in the nanochannel 10; and apply to a portion of the strand F present in the nanochannel 10 a force such as to cause stretching of the strand F itself, i.e., a condition in which consecutive bases are arranged at a greater distance apart from one another than in the case of absence of external forces.

As is shown in FIG. 4, the inlet well 12 is initially filled with a solution containing denatured nucleic acid strands, which have a negative electrical charge. The nanochannel 10 is occupied exclusively by the solution and is free from strands. The first electrical impedance Z' has a respective first (low) value. The control unit 20 sets the first voltage $V_1$ to a negative value and the second voltage $V_2$ to a first positive value, so as to favor entry into the nanochannel 10 of one end of one of the nucleic acid strands present in the inlet well 12 (FIG. 5). The value of the third voltage $V_3$ in this step is indifferent and, for example, may be equal to the value of the second voltage $V_2$.

When the end of a nucleic acid strand F enters a first portion of the nanochannel 10, comprised between the inlet well 12 and the control well 13, where the base-detection device 4 is located, the first electrical impedance Z' detected by the first impedance-meter stage 18 starts to increase. In response to the increase in the first electrical impedance Z', the control unit 20 sets the first voltage $V_1$ to a positive value and increases the second voltage $V_2$ up to a respective second value, higher than the positive value of the first voltage $V_1$. The positive value of the first voltage $V_1$ enables attraction of further denatured strands into the inlet well 12, for example from a loading reservoir not illustrated. The second voltage $V_2$, higher than the first voltage $V_1$, produces an electrostatic force that attracts the end of the strand F present in the nanochannel 10 towards the second electrode 16 and the control well 13. The portion of the strand F still in the inlet well 12 unwraps as the end proceeds along the nanochannel 10.

When the end of the strand F present in the nanochannel 10 reaches the second electrode 16 and the control well 13, the control unit 20 sets the third voltage $V_3$ on the third electrode 17 to a value higher than the value of the second voltage $V_2$ on the second electrode 16 (which is thus intermediate between the first voltage $V_1$ and the third voltage $V_3$), for feeding the nucleic acid strand F along a second portion of the nanochannel 10, comprised between the control well 13, where the base-detection device 4 is located, and the collection well 14.

Entry of the strand F into the second portion of the nanochannel 10 causes an increase of the second electrical impedance Z", which is detected by the second impedance-meter stage 9. In response to the increase in the second electrical impedance Z", the control unit 20 sets the values of the voltages $V_1$, $V_2$, $V_3$ so as to favor removal of any obstruction from the first portion of the nanochannel 10. In fact, even though introduction of a further nucleic acid strand into the nanochannel 10 already occupied is highly unlikely on account of the dimensions, an event of this type cannot be ruled out. In one embodiment, the control unit 20 thus applies forces that tend to remove an additional strand from the nanochannel 10 already occupied. In particular, the control unit 20 sets the third voltage $V_3$ to a value higher than both the first voltage $V_1$ and the second voltage $V_2$, and the first voltage $V_1$ to a value higher than the second voltage $V_2$ and thus intermediate between the second voltage $V_2$ and the third voltage $V_3$. In this way, the strand F that has already reached the second portion of the nanochannel 10 is withheld, because the higher contribution of the third voltage $V_3$ prevails. Any possible strands further present in the first portion of the nanochannel 10 are instead expelled, because the electrostatic force determined by the first voltage $V_1$ and by the second voltage $V_2$ pushes the nucleic acids, which are negatively charged, towards the inlet well 12. The nanochannel 10 is thus freed from the presence of any possible additional strands.

Once the procedure of removal of possible obstructions has been carried out, the control unit 20 sets once again the voltages $V_1$, $V_2$, $V_3$ so as to control advance and stretching of the strand F present in the nanochannel 10.

More precisely, the difference between the third voltage $V_3$ and the first voltage $V_1$ determines the speed and direction of advance of the nucleic acid strand F along the nanochannel 10. When the third voltage $V_3$ is higher than the first voltage $V_1$, the strand F proceeds from the inlet well 12 towards the collection well 14. When, instead, the third voltage $V_3$ is lower than the first voltage $V_1$, the nucleic acid strand F moves in the opposite direction, from the collection well 14 to the inlet well 12. The absolute value of the difference between the third voltage $V_3$ and the first voltage $V_1$ determines the speed of advance of the strand F.

The difference between the third voltage $V_3$ and the second voltage $V_2$, instead, causes stretching of the nucleic acid strand F that is advancing in the detection site. In the absence of applied external forces, consecutive bases of a nucleic acid strand are arranged apart from one another with an approximately constant pitch (around 0.33 nm). The electrostatic force due to the difference between the third voltage $V_3$ and the second voltage $V_2$ acts upon the extended strand F and causes a separation between consecutive bases, in particular, at the detection site. The distance between consecutive bases may thus be controlled and adapted for optimizing the performance and reliability of the base-detection device 4. Furthermore, if the base-detection device 4 is based upon hybridization of target oligonucleotides, it is possible to control the force on the strand F being examined for favoring hybridization and subsequently separate the strand F and the hybridized target oligonucleotide mechanically.

The conveying device 5 thus enables an extremely fine and flexible control of the movement of the nucleic acid strands along the nanochannel 10. The use of the three electrodes 15, 16, 17 in fact enables control not only of the direction and speed of advance, but also of the force exerted on the portion of the strand F being examined in the base-detection device 4.

Figure 8:
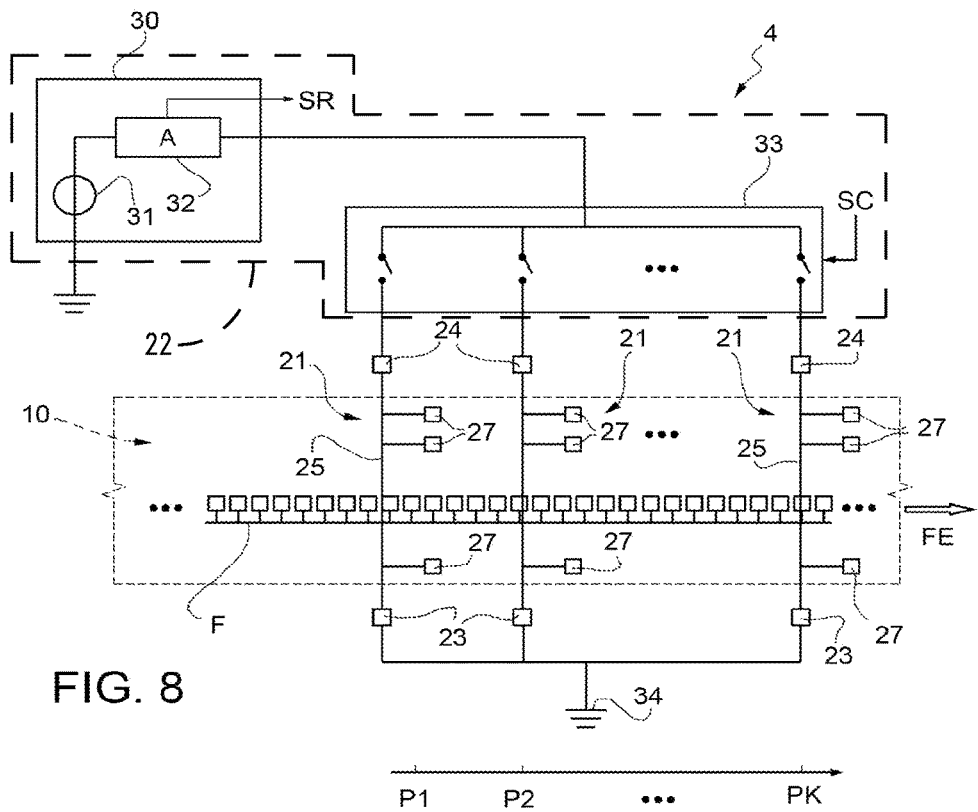
FIG. 8 is a more detailed block diagram of a portion of the apparatus of FIG. 1.

In one embodiment, the base-detection device 4 comprises a plurality of nanowire detectors 21 and a reading circuit 22, as is shown in FIG. 8. The nanowire detectors 21 are arranged in respective positions P1, P2, . . . PK along the nanochannel 10 at the detection site. Each nanowire detector 21 defines a field-effect device and comprises a source region 23, a drain region 24, and a nanowire 25, which connects the source region 23 and the drain region 24. The source region 23 and the drain region 24 are of semiconductor material having a first type of conductivity, for example N+, and are opposite with respect to a region of passage of the nucleic acid strands that are advancing in the detection site, in particular, with respect to the axis A of the nanochannel 10. The semiconductor material may for example be silicon, germanium, InP, GaN. The nanowire 25 is of the same semiconductor material as that of the source region 23 and drain region 24, but has a second type of conductivity, for example P. The nanowire 25 defines a channel region between the source region 23 and the drain region 24. The conductance of the nanowire 25 is determined by the presence of electrical charge around the nanowire 25 itself. In particular, a negative charge in the vicinity of the nanowire 25 causes a drop of the conductivity with respect to a condition of neutral charge.

The nanowires 25 of the nanowire detectors 21 are arranged in a direction transverse with respect to the axis A of the nanochannel 10 at the detection site so that a nucleic acid strand advancing along the nanochannel 10 itself will traverse the nanowires 25. In one embodiment, the nanowires 25 are parallel to one another and are arranged in succession along the nanochannel 10.

Each nanowire 25 is functionalized with respective nucleic acid probes 27. The nucleic acid probes 27 are defined by oligonucleotides with the same number N of bases, for example four. In one embodiment, the nucleic acid probes 27 have the structure of a peptidonucleic acid (PNA), which contains repeated units of N-(2-aminoethyl)-glycine joined by peptide bonds and is electrically neutral. Associated to each nanowire 25 are nucleic acid probes 27 of the same type (i.e., containing the same base sequences). Given that the nucleic acid probes 27 are electrically neutral, their presence does not modify the state of conduction of the respective nanowire detector 21. However, the nucleic acid probes 27 may hybridize to corresponding base sequences in the nucleic acid strands advancing in the nanochannel 10. In this case, the sequence of the hybridized nucleic acid is withheld in the proximity of the corresponding nanowire 25 and with its own negative charge causes an increase of impedance of the nanowire detector 21.

The nanowires 25 and the respective nucleic acid probes 27 exhaust the $4^N$ combinations that may be obtained with the number N of bases contained in each nucleic acid probe 27. In the example described, the possible combinations of four bases are $4^4=256$ and there are present as many nanowires 25, each with nucleic acid probe 27 of a respective type. Furthermore, each nanowire 25 occupies a respective position P1, P2, . . . , PK (where $K=4^N$ is the number of possible combinations of bases) along the nanochannel 10.

The reading circuit 22 is configured to determine the state of conduction of each of the nanowire detectors 21, for example by impedance detection. In one embodiment, the reading circuit 22 comprises an impedance-meter stage 30, for example including a voltage source 31 and a current sensor 32, and a multiplexer 33, configured to connect the impedance-meter stage 30 selectively to one of the nanowire detectors 21, in particular, to the drain region 24 (the source regions 23 of the nanowire detectors 21 are connected to a reference-potential line 34, for example a ground line).

As has been mentioned, when the nucleic acid probes 27 of one of the nanowire detectors 21 hybridize a corresponding sequence of the nucleic acid strand F advancing in the nanochannel 10, the negative charge of the strand F causes an increase of impedance of the nanowire 10, which is detected by the impedance-meter stage 30.

Figure 9:
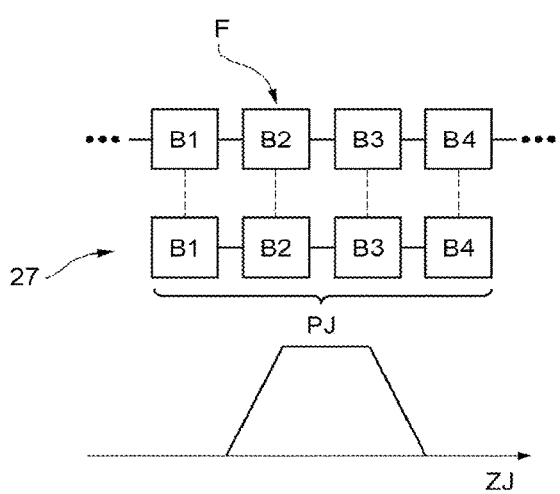
FIGS. 9-11 are graphs that show electrical quantities regarding the apparatus of FIG. 1.

The control unit 20 queries the base-detection device 4, which, in response to the queries, supplies information regarding the bases of the nucleic acid strand F advancing in the nanochannel 10. In detail, the control unit controls the multiplexer 33 by a control signal SC so as to connect the impedance-meter stage 30 in rotation to each of the nanowire detectors 21, and receives in response a read signal SR indicating the state of conduction of the nanowire detectors 21 connected to the impedance-meter stage 30 and, consequently, the presence of the respective set of bases in the portion of the nucleic acid strand F that is advancing in the detection site. More precisely, an increase of impedance of one of the nanowire detectors 21 (for example, in position PJ) indicates the presence of a respective sequence of bases (four, in the example described) in the portion of the nucleic acid strand F that is advancing in the detection site, as illustrated in FIG. 9. The succession of the read signals SR defines the raw sequence supplied by the base-detection device 4.

Figures 10, 11:
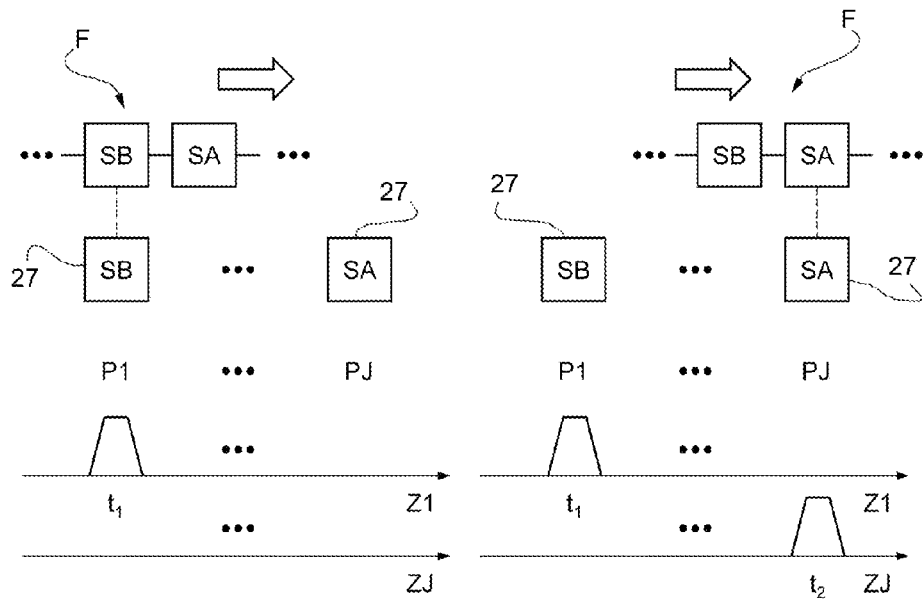

The control unit 20 reconstructs the effective base sequence SEQ that forms the nucleic acid strand F on the basis of the read signals SR received, taking into account the instants at which the read signals SR are generated and the positions P1, P2, . . . , PK occupied by the respective nanowires 25 along the nanochannel 10. In one embodiment, each sequence of bases recognized by the base-detection device 4 is translated, in the effective base sequence SEQ, by a number of positions such as to compensate the detection delay due to the distance between the generic position PJ of the hybridized nanowire detector 21, which has positively made a detection, and the position P1 of the first nanowire detector 21 reached by the nucleic acid strand F. For instance, if the nucleic acid strand F that is advancing in the detection site contains a sequence SA of N bases that may be detected by the nanowire detector 21 in position PJ, followed by a sequence SB of N bases that may be detected by the nanowire detector 21 in position P1, the base-detection device 4 recognizes the sequence SB before the sequence SA (FIGS. 10 and 11: the impedance Z1 of the nanowire detector 21 corresponding to the sequence SA increases before the impedance ZJ of the nanowire detector 21 corresponding to the sequence SB). The control unit 20 re-aligns the sequences SA and SB and compensates the delay with a relative shift of J−1 positions of the sequence SB with respect to the sequence SA. Re-alignment may be obtained either by translating the sequence SB J−1 positions forwards or by translating the sequence SA J−1 positions backwards. More in general, re-alignment between a sequence detectable by the nanowire detector 21 in position PI and a sequence detectable by the nanowire detector 21 in position PJ (J>I) is obtained with a relative shift of J−I−1 positions in the effective base sequence SEQ. Translation in the effective base sequence SEQ of the raw sequence of the read signals SR may be obtained, for example, by entering the base sequences corresponding to the read signals SR into a shift register in positions translated with respect to a reference position as a function of the position of the nanowire detector 21.

The control unit 20 may also take into account possible overlaps in the sequences recognized by the base-detection device 4. For instance, a sequence containing the bases AAAAC may be recognized both by the nanowire detector 21 associated to which are nucleic acid probes 27 with the sequence AAAA and by the nanowire detector 21 associated to which are nucleic acid probes 27 with the sequence AAAC. The overlapping portion (in this case AAA) may be used as check on the correctness of recognition.

The conveying device 5 described with reference to FIGS. 1-7 enables control of the conditions in which the strand F interacts with the base-detection device 4. In particular, in the case of the base-detection device 4 based upon nanowire detectors, the conveying device enables determination both of the speed at which the strand F travels in the proximity of the nanowire detectors 21 and the force applied on the strand F itself. It is thus possible to control with high accuracy the hybridization conditions and the separation of the nucleic acid probes 27 and of the nucleic acid strand F in the nanochannel 10.

Finally, it is evident that modifications and variations may be made to the device and to the method described, without thereby departing from the scope of the present disclosure.

Figure 12:
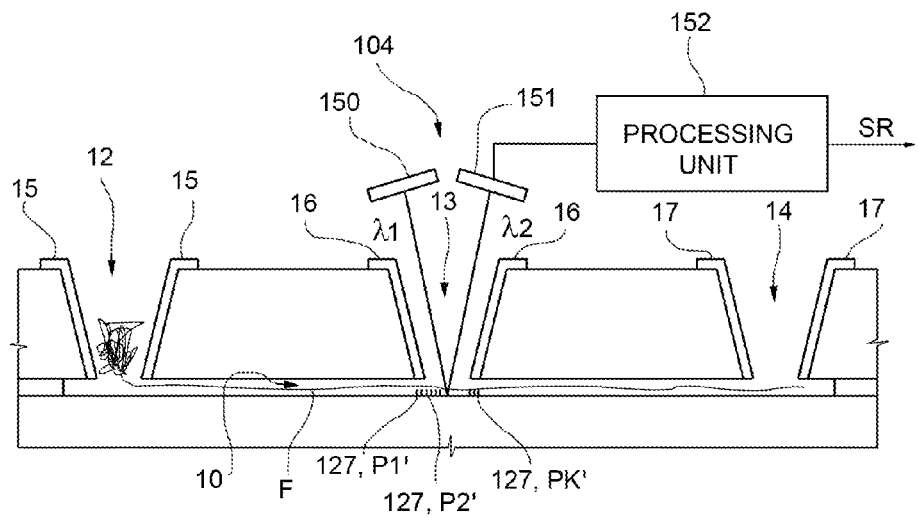
FIG. 12 is a cross-section through a body integrating a portion of an apparatus for nucleic acid sequencing according to a different embodiment of the present disclosure.

The base-detection device may exploit a different operating principle. For instance, in the embodiment of FIG. 12, a base-detection device 104 of an optical type is used, which comprises nucleic acid probes 127 fixed to a wall of the nanochannel 10 in respective detection positions P1', P2', . . . , PK'. Fluorescent pigments are available in the solution present in the nanochannel and are incorporated in the nucleic acid probes 127 hybridized with corresponding sequences of the nucleic acid strand advancing in the nanochannel. The hybridized nucleic acid probes 127 are then selectively excited by light radiation at a first wavelength $\lambda 1$, supplied by a light source 150, and emit in response light radiation at a second wavelength $\lambda 2$. The radiation emitted by the nucleic acid probes 127 at the second wavelength $\lambda 2$ is received by an image sensor 151. The images captured by the image sensor 151 are processed by a processing unit 152, which recognizes base sequences in the nucleic acid strand advancing in the nanochannel on the basis of the presence or to the absence of radiation at the second wavelength $\lambda 2$ in the detection positions P1', P2', . . . , PK'. The inspection of the nucleic acid probes may be carried out through the control well 13, which enables optical access to the nanochannel 10.

Figure 13:
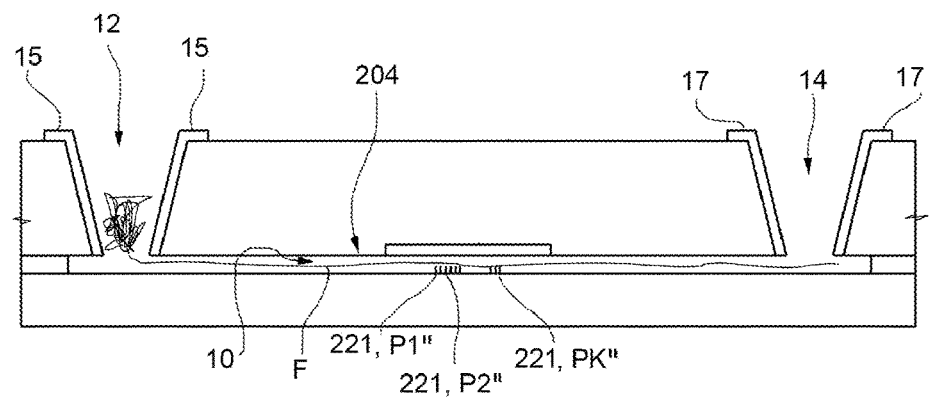
FIG. 13 is a cross-section through a body integrating a portion of an apparatus for nucleic acid sequencing according to a further embodiment of the present disclosure.
Figure 14:
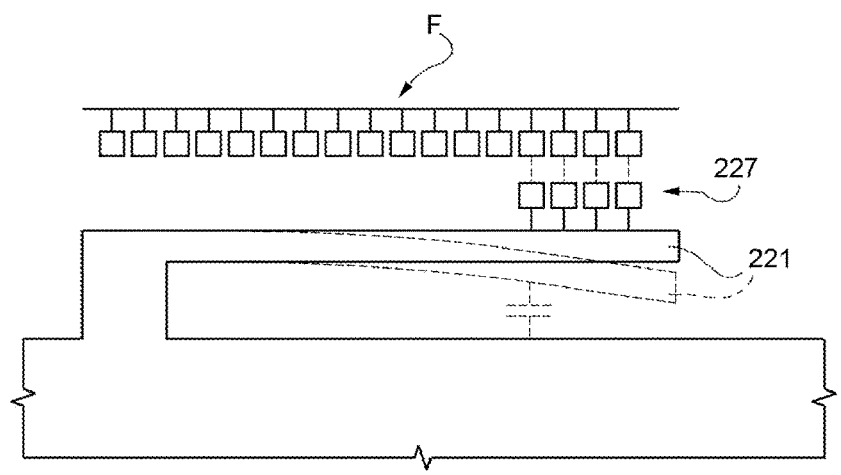
FIG. 14 shows an enlarged detail of the apparatus of FIG. 13.

In a further embodiment, illustrated in FIGS. 13 and 14, a base-detection device 204 is of the cantilever type. In this case, the nucleic acid probes 227 are fixed to cantilever detection electrodes 221, the configuration of which changes when the respective nucleic acid probes 227 are bound to corresponding sequences of the strand advancing in the nanochannel. In particular, the charge associated to the strand F causes a deformation of the cantilever detection electrode 221, which may in turn alter the capacitance of a capacitor or bring about opening or closing of a circuit.

In addition, in apparatuses that use a base-detection device not of an optical type, the intermediate control well between the inlet well and the collection well may be absent. In these cases, the control electrode may be integrated in the first structural layer or in the second structural layer.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An apparatus for nucleic acid sequencing, comprising:
a nanochannel; and
a first electrode, a second electrode, and a third electrode arranged along the nanochannel so as to be in contact with a fluid occupying the nanochannel, the second electrode being arranged between the first electrode and the third electrode; wherein:
the nanochannel has a length and transverse dimensions, in directions perpendicular to the length, such as to enable entry of one end of a single nucleic acid strand in the fluid and prevent entry of further strands of nucleic acid when the nanochannel is occupied.

2. The apparatus according to claim 1, comprising:
a first presence sensor configured to detect whether the nucleic acid strand is present in a first portion of the nanochannel, between the first electrode and the second electrode; and
a second presence sensor configured to detect whether the nucleic acid strand is present in a second portion of the nanochannel, between the second electrode and the third electrode.

3. The apparatus according to claim 2, wherein:
the first presence sensor includes a first impedance meter configured to determine a first electrical impedance between the first electrode and the second electrode; and
the second presence sensor includes a second impedance meter configured to determine a second electrical impedance between the second electrode and the third electrode.

4. The apparatus according to claim 1, comprising a base-detection device set in a detection site and configured to detect bases of a portion of the nucleic acid strand that is advancing in the detection site.

5. An apparatus for nucleic acid sequencing, comprising:
a nanochannel;
a first electrode, a second electrode, and a third electrode arranged along the nanochannel so as to be in contact with a fluid occupying the nanochannel, the second electrode being arranged between the first electrode and the third electrode; and
a base-detection device set in a detection site and configured to detect bases of a portion of a nucleic acid strand that is advancing in the detection site, wherein the base-detection device comprises a plurality of field-effect detectors, each including a respective nanowire and nucleic acid probes associated with the nanowire, the nucleic acid probes of each of the field-effect detectors being defined by a sequence of bases and fixed to the associated nanowire.

6. The apparatus according to claim 5, wherein:
the nanowires of the field-effect detectors are parallel to one another and are arranged in succession along the nanochannel,
for each nanowire, the nucleic acid probes associated the nanowire have a type that is distinct from types of the nucleic acid probes associated with others of the nanowires, and
all the nucleic acid probes have the same number of bases.

7. A method for nucleic acid sequencing, comprising:
introducing one end of a nucleic acid strand into a nanochannel containing a solution;
controlling motion of the nucleic acid strand along the nanochannel; wherein controlling motion of the nucleic acid strand comprises applying a first voltage, a second voltage, and a third voltage, respectively, to a first electrode, to a second electrode, and to a third electrode, arranged along the nanochannel so as to be in contact with a fluid occupying the nanochannel, the second electrode being arranged between the first electrode and the third electrode;
detecting whether the nucleic acid strand is in a first portion of the nanochannel, between the first electrode and the second electrode, and
detecting whether the nucleic acid strand is in a second portion of the nanochannel between the second electrode and the third electrode.

8. The method according to claim 7, wherein controlling motion of the nucleic acid strand comprises setting a negative value of the first voltage and a positive value of the second voltage when the first portion of the nanochannel is free.

9. The method according to claim 7, wherein controlling motion of the nucleic acid strand comprises setting a value of the first voltage and a value of the second voltage, higher than the value of the first voltage, when the first portion of the nanochannel is occupied by the nucleic acid strand and the second portion of the nanochannel is free of the nucleic acid strand.

10. The method according to claim 7, wherein controlling motion of the nucleic acid strand comprises setting a value of the first voltage, a value of the third voltage higher than the value of the first voltage, and a value of the second voltage intermediate between the value of the first voltage and the value of the third voltage, when the first portion of the nanochannel and the second portion of the nanochannel are occupied by the nucleic acid strand.

11. The method according to claim 7, wherein controlling motion of the nucleic acid strand comprises setting a value of the first voltage, a value of the third voltage lower than the value of the first voltage, and a value of the second voltage intermediate between the value of the first voltage and the value of the third voltage, when the first portion of the nanochannel and the second portion of the nanochannel are occupied by the nucleic acid strand.

12. The method according to claim 7, wherein controlling motion of the nucleic acid strand comprises setting a value of the first voltage, a value of the third voltage higher than the value of the first voltage, and a value of the second voltage lower than the value of the first voltage, when the first portion of the nanochannel and the second portion of the nanochannel are occupied by the nucleic acid strand.

13. A method for nucleic acid sequencing, comprising:
introducing one end of a nucleic acid strand into a nanochannel containing a solution;
controlling motion of the nucleic acid strand along the nanochannel; wherein controlling motion of the nucleic acid strand comprises:
applying a first voltage, a second voltage, and a third voltage, respectively, to a first electrode, to a second electrode, and to a third electrode, arranged along the nanochannel so as to be in contact with a fluid occupying the nanochannel, the second electrode being arranged between the first electrode and the third electrode; and
setting a negative value of the first voltage and a positive value of the second voltage when the first portion of the nanochannel is free.

14. The method according to claim 13, wherein controlling motion of the nucleic acid strand comprises setting a value of the first voltage and a value of the second voltage, higher than the value of the first voltage, when the first portion of the nanochannel is occupied by the nucleic acid strand and the second portion of the nanochannel is free of the nucleic acid strand.

15. A method for nucleic acid sequencing, comprising:
introducing one end of a nucleic acid strand into a nanochannel containing a solution;
controlling motion of the nucleic acid strand along the nanochannel; wherein controlling motion of the nucleic acid strand comprises:
applying a first voltage, a second voltage, and a third voltage, respectively, to a first electrode, to a second electrode, and to a third electrode, arranged along the nanochannel so as to be in contact with a fluid occupying the nanochannel, the second electrode being arranged between the first electrode and the third electrode; and
setting a value of the first voltage and a value of the second voltage, higher than the value of the first voltage, when the first portion of the nanochannel is occupied by the nucleic acid strand and the second portion of the nanochannel is free of the nucleic acid strand.

16. The method according to claim 15, wherein controlling motion of the nucleic acid strand comprises setting a value of the first voltage, a value of the third voltage higher than the value of the first voltage, and a value of the second voltage intermediate between the value of the first voltage and the value of the third voltage, when the first portion of the nanochannel and the second portion of the nanochannel are occupied by the nucleic acid strand.

17. A method for nucleic acid sequencing, comprising:
introducing one end of a nucleic acid strand into a nanochannel containing a solution;
controlling motion of the nucleic acid strand along the nanochannel; wherein controlling motion of the nucleic acid strand comprises:
applying a first voltage, a second voltage, and a third voltage, respectively, to a first electrode, to a second electrode, and to a third electrode, arranged along the nanochannel so as to be in contact with a fluid occupying the nanochannel, the second electrode being arranged between the first electrode and the third electrode; and
setting a value of the first voltage, a value of the third voltage higher than the value of the first voltage, and a value of the second voltage intermediate between the value of the first voltage and the value of the third voltage, when the first portion of the nanochannel and the second portion of the nanochannel are occupied by the nucleic acid strand.

18. The method according to claim 17, wherein controlling motion of the nucleic acid strand comprises setting a value of the first voltage, a value of the third voltage lower than the value of the first voltage, and a value of the second voltage intermediate between the value of the first voltage and the value of the third voltage, when the first portion of the nanochannel and the second portion of the nanochannel are occupied by the nucleic acid strand.

19. A method for nucleic acid sequencing, comprising:
introducing one end of a nucleic acid strand into a nanochannel containing a solution;
controlling motion of the nucleic acid strand along the nanochannel; wherein controlling motion of the nucleic acid strand comprises:
applying a first voltage, a second voltage, and a third voltage, respectively, to a first electrode, to a second electrode, and to a third electrode, arranged along the nanochannel so as to be in contact with a fluid occupying the nanochannel, the second electrode being arranged between the first electrode and the third electrode; and
setting a value of the first voltage, a value of the third voltage lower than the value of the first voltage, and a value of the second voltage intermediate between the value of the first voltage and the value of the third voltage, when the first portion of the nanochannel and the second portion of the nanochannel are occupied by the nucleic acid strand.

20. The method according to claim 19, wherein controlling motion of the nucleic acid strand comprises setting a negative value of the first voltage and a positive value of the second voltage when the first portion of the nanochannel is free.

21. A method for nucleic acid sequencing, comprising:
introducing one end of a nucleic acid strand into a nanochannel containing a solution;
controlling motion of the nucleic acid strand along the nanochannel; wherein controlling motion of the nucleic acid strand comprises:
applying a first voltage, a second voltage, and a third voltage, respectively, to a first electrode, to a second electrode, and to a third electrode, arranged along the nanochannel so as to be in contact with a fluid occupying the nanochannel, the second electrode being arranged between the first electrode and the third electrode; and
setting a value of the first voltage, a value of the third voltage higher than the value of the first voltage, and a value of the second voltage lower than the value of the first voltage, when the first portion of the nanochannel and the second portion of the nanochannel are occupied by the nucleic acid strand.

22. The method according to claim 21, wherein controlling motion of the nucleic acid strand comprises setting a negative value of the first voltage and a positive value of the second voltage when the first portion of the nanochannel is free.

23. An apparatus for nucleic acid sequencing, comprising:
a structural body having a first portion and a second portion;
a nanochannel positioned in the structural body and between the lower and upper portion; and
a first electrode, a second electrode, and a third electrode arranged along the nanochannel so as to be in contact with a fluid occupying the nanochannel, the second electrode being arranged between the first electrode and the third electrode;
the first portion of the structural layer includes a surface that defines a first side of the nanochannel, the surface being continuous along an entire length of the nanochannel;
the second portion of the structural layer includes a surface that defines a second side of the nanochannel, the second side being opposite to the first side;
the second portion of the structural layer includes first, second, and third wells that are open to the nanochannel and house the first, second, and third electrodes, respectively.

24. The apparatus according to claim 23, further comprising:
   a first presence sensor configured to detect whether the nucleic acid strand is present in a first portion of the nanochannel, between the first electrode and the second electrode; and
   a second presence sensor configured to detect whether the nucleic acid strand is present in a second portion of the nanochannel, between the second electrode and the third electrode.

25. The apparatus according to claim 23, further comprising:
   a base-detection device set in a detection site and configured to detect bases of a portion of the nucleic acid strand that is advancing in the detection site, wherein the base-detection device comprises a plurality of field-effect detectors, each including a respective nanowire and nucleic acid probes associated with the nanowire, the nucleic acid probes of each of the field-effect detectors being defined by a sequence of bases and fixed to the associated nanowire.

\* \* \* \* \*